US010597601B2

(12) United States Patent
Heiska et al.

(10) Patent No.: US 10,597,601 B2
(45) Date of Patent: Mar. 24, 2020

(54) METHOD FOR RECOVERING LIPIDS FROM MICROBIAL BIOMASS

(71) Applicant: NESTE OYJ, Espoo (FI)

(72) Inventors: Arto Heiska, Helsinki (FI); Annika Malm, Helsinki (FI); Jukka-Pekka Pasanen, Helsinki (FI)

(73) Assignee: NESTE OYJ, Espoo (FI)

( * ) Notice: Subject to any disclaimer, the term of this patent is extended or adjusted under 35 U.S.C. 154(b) by 122 days.

(21) Appl. No.: 15/319,686

(22) PCT Filed: Jun. 16, 2015

(86) PCT No.: PCT/FI2015/050437
§ 371 (c)(1),
(2) Date: Dec. 16, 2016

(87) PCT Pub. No.: WO2015/193547
PCT Pub. Date: Dec. 23, 2015

(65) Prior Publication Data
US 2017/0137742 A1    May 18, 2017

(30) Foreign Application Priority Data

Jun. 17, 2014 (EP) .................................. 14172853

(51) Int. Cl.
| | | |
|---|---|---|
| *C11B 1/08* | (2006.01) | |
| *C11B 1/14* | (2006.01) | |
| *C11B 1/02* | (2006.01) | |
| *C11B 1/10* | (2006.01) | |
| *C12P 7/64* | (2006.01) | |
| *C10L 5/44* | (2006.01) | |
| *C10L 1/02* | (2006.01) | |
| *C10L 9/08* | (2006.01) | |
| *A23K 20/147* | (2016.01) | |
| *C07K 14/39* | (2006.01) | |

(52) U.S. Cl.
CPC .............. *C11B 1/08* (2013.01); *A23K 20/147* (2016.05); *C07K 14/39* (2013.01); *C10L 1/02* (2013.01); *C10L 5/445* (2013.01); *C10L 9/086* (2013.01); *C11B 1/02* (2013.01); *C11B 1/10* (2013.01); *C11B 1/108* (2013.01); *C11B 1/14* (2013.01); *C12P 7/6463* (2013.01); *C10L 2290/08* (2013.01); *C10L 2290/26* (2013.01); *C10L 2290/544* (2013.01); *C10L 2290/547* (2013.01); *Y02E 50/10* (2013.01); *Y02E 50/30* (2013.01)

(58) Field of Classification Search
None
See application file for complete search history.

(56) References Cited

U.S. PATENT DOCUMENTS

| | | | |
|---|---|---|---|
| 6,441,208 B2 † | 8/2002 | Bijl | |
| 2003/0014369 A1 | 1/2003 | Okayama et al. | |
| 2003/0143659 A1 | 7/2003 | Bijl et al. | |
| 2009/0226993 A1* | 9/2009 | Kumar | C12N 1/16 435/165 |
| 2012/0079760 A1* | 4/2012 | Savage | C10L 1/026 44/388 |
| 2012/0116105 A1* | 5/2012 | Aaltonen | C11B 1/10 554/20 |
| 2014/0234919 A1* | 8/2014 | Yu | C12P 7/6463 435/134 |

FOREIGN PATENT DOCUMENTS

| | | |
|---|---|---|
| EP | 2450424 A1 | 5/2012 |
| EP | 2450426 A1 | 5/2012 |
| WO | 2011/143380 A2 | 11/2011 |

OTHER PUBLICATIONS

Ryu et al., "High-cell-density cultivation of oleaginous yeast Cryptococcus curvatus for biodiesel production using organic waste from the brewery industry", Bioresource Technology, vol. 135, pp. 357-364. (Year: 2013).*
International Search Report (ISR) & Written Opinion dated Oct. 9, 2015, for PCT/FI2015/050437.
Extended European Search Report dated Nov. 13, 2017, for EP 15809946.5-1501 / 3158035.
Miao, C. et al., "Sequential hydrothermal fractionation of yeast Cryptococcus curvatus biomass." Bioresource Technology, 2014, vol. 164, pp. 106-112.
Espinosa-Gonzalez, I. et al., "Hydrothermal treatment of oleaginous yeast for the recovery of free fatty acids for use in advanced biofuel production." Journal of Biotechnology, 2014, vol. 187, pp. 10-15.
Milanesio, J. et al., "Extraction of lipids from Yarrowia Lipolytica." Journal of Chemical Technology and Biotechnology, Mar. 2013, vol. 88, No. 3, pp. 378-387.
Hammerschmidt, A. et al., "Conversion of yeast by hydrothermal treatment under reducing conditions." Fuel, IPC Science and Technology Press, Guildford, GB, vol. 90, No. 11, pp. 3424-3432, Jun. 15, 2011.
Farr, W. E. and Proctor, A., Green Vegetable Oil Processing, 2012, AOCS Press (abstract and table of contents only).
Davies, R., "Scale Up of Yeast Oil Technology." Industrial Applications of Single Cell Oils. Edited by: D. J. Kyle and C. Ratledge, 1992, AOCS Publishing.
Pedersen, M. and Meyer, A. S., "Lignocellulose pretreatment severity— relating pH to biomatrix opening." New Biotechnology vol. 27, No. 6, pp. 739-750, 2010.

(Continued)

*Primary Examiner* — Michelle F. Paguio Frising
(74) *Attorney, Agent, or Firm* — Buchanan Ingersoll & Rooney PC

(57) ABSTRACT

A method is disclosed for recovering lipids from microbial biomass, and for producing lipids. In the method, an aqueous suspension includes fermentation broth containing oleaginous yeast biomass which is subjected to hydrothermal treatment and lipids are recovered from the biomass by solvent extraction.

21 Claims, No Drawings

(56) References Cited

OTHER PUBLICATIONS

Levine, Robert B., Tanawan Pinnarat, and Phillip E. Savage. "Biodiesel production from wet algal biomass through in situ lipid hydrolysis and supercritical transesterification." Energy & Fuels 24.9 (2010): 5235-5243.†

Tsigie, Yeshitila Asteraye, et al. "Maximizing biodiesel production from Yarrowia lipolytica Po1g biomass using subcritical water pretreatment." Bioresource technology 111 (2012): 201-207.†

\* cited by examiner
† cited by third party

METHOD FOR RECOVERING LIPIDS FROM MICROBIAL BIOMASS

FIELD OF THE INVENTION

The present invention relates to a method for recovering lipids from microbial biomass and to a method for producing lipids using the method for recovering lipids.

BACKGROUND OF THE INVENTION

Certain microorganisms such as bacteria, fungi and yeasts are known to convert organic molecules to lipids. Oil produced by heterotrophic microorganisms is often called as single cell oil or microbial oil and lipid producing microorganisms are called oleaginous microbes.

Process for production of single cell oil typically comprises steps of cultivating microorganisms, allowing cells to accumulate lipids, harvesting lipid-rich cells and recovering lipid from microbial cells. Microorganism-based lipids (i.e. single cell oils) can be used as raw materials for production of biofuels such as biodiesel, renewable diesel or bio jet fuel.

The oleaginous microorganisms cultivated on a growth medium can contain lipids up to 80% of their total dry matter content. The efficiency of the method used to recover lipids from microbial biomass is crucial to the economically feasible production of biofuels by microbial fermentation. The method used for lipid recovery should provide around 95% oil yield in order to be economically feasible. Furthermore, the method used to recover the lipids should not destroy the value of the residual biomass, from which oil has been extracted or to decrease the quality of the extracted oil, which can be further processed or used as such.

A lipid recovery process typically comprises steps of harvesting the microbial cells from cultivation medium, disrupting the microbial cells and recovery of oil to obtain crude microbial oil and a residual biomass fraction. The oil can be recovered from wet biomass or in case of dry extraction, the microbial biomass is dewatered before oil recovery. The residual biomass fraction may be used as animal feed since it contains valuable protein fractions or used for energy production through combustion. The method to recover lipids basically determines the value of the residual biomass as animal feed since the proteins of microbial biomass are easily degraded during the various process steps.

The harvesting step is used to separate microbial cells from cultivation medium. Conventional harvesting techniques include filtration and centrifugation. The microbial biomass can also be concentrated before drying step by mechanical dewatering means before the recovery of lipids.

Oil is usually recovered from the harvested microbial cells by extraction with a solvent such as carbon dioxide in subcritical or supercritical state or liquid hydrocarbons such as hexane. Microbial cells may also be disrupted before extraction of lipids with methods such as ultra-sonication, osmotic shock, mechanical shear force such as extrusion, cold press, and thermal shock. The need to completely disrupt the microbial cells depends on the solvent used to extract lipids. In case complete disruption of cells is not possible, a mixture of non-polar and polar solvents can be used in extraction.

In dry extraction the harvested biomass is dried before solvent extraction to remove as much free water as possible. The lipids can also be extracted from wet biomass. In the dry extraction the microbial biomass is typically dried to a dry matter content of above 90% before solvent extraction. In wet route extraction the dry matter content of the biomass can be as low as 5% in the solvent extraction step. In case of wet extraction the resulting wet residual biomass fraction needs to be dried if it is used in value added applications.

Traditional cell harvesting techniques such as filtration and centrifugation usually result in a biomass with dry matter contents from 15% up to 40%. The dry matter content of harvested biomass can be further increased by drying, which, however, consumes a lot of energy. Drying can be performed by heating, freeze drying or spray drying (Farr, W. E. and Proctor, A., Green Vegetable Oil Processing, 2012, AOCS Press). Generally biomasses having dry matter contents of below 30 w-% are not considered economical to dry.

The selection between dry and wet route extraction depends on the ease of removal of excess liquid from microbial biomass. Wet route extraction is usually preferred if biomass cannot be dewatered mechanically to above 30% dry mater content. Wet extraction is also preferred if the subsequent processing of the residual biomass does not require further drying, e.g. if biomass is to be processed by anaerobic digestion or by hydrothermal liquefaction.

The ease of removal of water from wet microbial biomass depends on the type of microorganisms in the microbial biomass. Filamentous organisms are considered much easier to harvest due to their large cell size whereas algal biomass is known to have poor filterability due to the small cell size. Wet route extraction has been suggested as an efficient lipid recovery method for algal biomass in EP2450424A1 as it is clearly stated that it is not necessary to dry the wet microbial biomass before extraction. Thus EP2450424A1 does not relate to the filtration and drying steps before extraction. Moreover, the document refers to an elevated pressure of the extraction itself since propane is used which requires a pressure of at least 20 bar during the extraction step in order to keep the extractant/solvent in liquid state. With respect to the heating step, there is no mentioning of the exact pressures used. The examples according to the document reveals rather low yields of lipids using the method as disclosed in the document and there is no mentioning of the content of nitrogen in the extracted oils from the biomass.

Water present in the harvested cells is known to decrease the efficiency of the solvent extraction since it shields the hydrophobic lipids from solvent contact. Additionally, water tends to form emulsions with the solvent, which furthermore decreases the extraction efficiency and makes it more difficult to separate extracted lipids from the rest of the liquid phase. Consequently, the dry extraction is usually preferred over wet extraction if the microbial biomass can be mechanically dewatered to above 30% dry matter content.

It is has been previously disclosed by Davies (Davies, R. 1992. Scale Up of Yeast Oil Technology. Industrial Applications of Single Cell Oils. Edited by: D. J. Kyle and C. Ratledge, AOCS Publishing) that a nozzle disc separator, which is typically used in the brewing and baker's yeast industry to harvest yeast, is not efficient for harvesting oleaginous yeast when the oil content of the biomass is over 35% on a dry weight basis. With oleaginous yeast biomasses that have higher oil content than 35% on a dry weight basis, cross flow filtration has been suggested. However, this harvesting method has the disadvantage of low flux and membrane fouling, which mean that large membrane areas are needed.

Even if nozzle disc separator is used to harvest oleaginous yeast with oil content under 35% on a dry weight basis, the resulting concentrated yeast cream has a dry matter content of 15-20%. This is universally deemed too low dry matter content for the drying to be economical. For this reason, the wet extraction is commonly preferred with oleaginous yeast with oil content lower than 35% on a dry weight basis harvested using a nozzle disc separator.

WO2011/143380 discloses a method for separation of oil from algal cells, in which method wet algal biomass is subjected to hydrothermal carbonization treatment (HTC), the resulting combined oil and char fraction are separated from aqueous fraction by filtration, and the oil is separated from char fraction by solvent extraction. The hydrothermal carbonization treatment is conducted at a temperature of from 170 to 225° C. The method has the advantage that it produces an aqueous fraction rich in nitrogen, phosphorus, and potassium, which can be reused in the growth stage as nutrients. The hydrothermal carbonization treatment is not reported to have any effect on filterability of the biomass or to efficiency of the extraction step. However, the document appears to exemplify methods based on process distiller grains and other raw materials. This type of raw material does not contain much lipids and as such would not present any difficulties in filtering the wet biomass where the method does not include a thermal treatment step prior to filtration. Moreover, in order to achieve high yield of the fatty acid methyl esters (FAMEs) it is necessary to both extract the dry char as well as the aqueous filtrate. Moreover, the reference is silent with respect to the quality of the retrieved oils with respect to e.g. nitrogen or phosphorus contents. In fact, the document clearly states that the aqueous product contains most of the nitrogen, phosphorus and potassium originally present in the biomass and extracting the aqueous phase would dearly result in a nitrogen content in level with the nitrogen content of the original biomass.

Microbial biomass is also commonly pasteurized in the harvesting step in order to kill the microorganisms and deactivate enzymes, which might otherwise destroy the lipid structures. In the method disclosed in US 2003/0143659, the pasteurization is conducted by heating the biomass in its growth medium to a temperature of 60-100° C. for up to 90 minutes. The pasteurization was not reported to have any effect on subsequent dewatering or lipid extraction steps.

EP2450426 relates to a purification method for purifying lipid materials already obtained from biological material. The method comprises the use of at least one polar solvent and at least one non-polar solvent and demonstrates how various reaction conditions influence the contents of phosphorus and metals in the purified oils. However, the document is silent with respect to the nitrogen content of the extracted oils and is also silent with respect to any methods of extracting oils from a biomass or how any conditions during extraction may influence the contents of e.g. nitrogen in the extracted oils.

The present invention is related to recovery of lipids from oleaginous yeast biomass and to a method for producing lipids using the method for recovery of lipids.

Davies (Davies, R. 1992. Scale Up of Yeast Oil Technology. Industrial Applications of Single Cell Oils. Edited by: D. J. Kyle and C. Ratledge, AOCS Publishing) reports poor recovery of oleaginous yeast cells, when the lipid content of the biomass exceeds 35% on a dry weight basis.

Harvesting of oleaginous yeast cells with dead end micro filters was found to be impossible due to the immediate blinding of filter membranes due to the soft cell structure of yeast biomass. The experiments also indicated that it was possible to harvest oleaginous yeast cells with a cross flow filtration arrangement but the filtration result was poor with only 28% dry matter content of harvested biomass, which is generally considered too low for the subsequent drying step. It was also found out that the presence of lignocellulosic material or remains of lignocellulosic material in the biomass suspension to be harvested makes the fouling of the membranes even worse.

Consequently, there is need for an effective method for recovery of lipids from oleaginous yeast biomass and especially from yeast biomasses having high lipid content, i.e. over 35% on a dry weight basis, such as e.g. at least about 40% on a dry weight basis, or such as e.g. at least about 50% on a dry weight basis, such as e.g. at least about 60% on a dry weight basis, such as e.g. at least about 70% on a dry weight basis, such as e.g. at least about 80% on a dry weight basis

SUMMARY OF THE INVENTION

One object of the present invention is to provide an effective method for recovery of lipids from oleaginous yeast biomass.

Accordingly, a first aspect of the present invention relates to a method for recovery of microbial lipids from oleaginous yeast biomass, said method comprising the steps of:
  (i) providing an aqueous suspension comprising fermentation broth containing oleaginous yeast biomass,
  (ii) subjecting said suspension to a hydrothermal treatment at a temperature of at least 160° C. for 1 second to 360 minutes at a pressure above 5 bar,
  (iii) subjecting the hydrothermally treated suspension to a separation step to obtain a liquid fraction and a yeast biomass fraction.
  (iv) subjecting the yeast biomass fraction to a drying step to obtain a dried yeast biomass fraction,
  (v) subjecting the dried biomass fraction to an extraction step with a liquid solvent to produce a liquid fraction comprising microbial lipids and a solid fraction comprising residual yeast biomass fraction,
  (vi) recovering the microbial lipids from the liquid fraction of step (v)
  (vii) optionally, isolating the residual biomass fraction from the product of step (v).

A second object of the present invention is to provide a method for production of microbial lipids with oleaginous yeasts using the method for recovery of lipids from oleaginous yeast biomass.

Accordingly, a second aspect of the present invention relates to a method for production of microbial lipids, the method comprising
  (i) providing a cultivation medium
  (ii) providing a fermentation broth by inoculating the cultivation medium with an oleaginous yeast to produce oleaginous yeast biomass,
  (iii) incubating said medium inoculated with said oleaginous yeast allowing lipid to accumulate,
  (iv) recovering microbial lipids from said oleaginous yeast biomass with the method according to any of the method for recovery of microbial lipids described herein.

A further aspect of the present invention relates to the residual biomass obtainable from the method of the present inventions.

Yet a further aspect of the present invention relates to microbial lipids obtainable by the method of the present invention.

In contrast to prior art, present invention minimizes the amount of water before extraction. This has the advantage that the extraction is conducted more efficiently with dried biomass since water is known to form emulsions with lipids, which disturbs the extraction step with an organic solvent and making separation of the organic phase from the liquid/aqueous phase difficult. Moreover, by the procedures of present invention, a more energy efficient method is provided since as much water as possible is removed by filtration prior to the drying of the resulting biomass.

Present invention also relates to extraction of the dried biomass without the need of any extraction of the separated liquid fraction.

Furthermore, by the method of present invention provides high quality oil which e.g. relates to a low nitrogen content of the extracted oils. This is important from the perspective of the further process of the retrieved oils as a high content of impurities such as e.g. nitrogen will hamper the catalytic process of the retrieved oils into fuels. This is also true with respect to impurities such as e.g. metal residues in the extracted oil. It is to be understood that the meaning of low levels of e.g. nitrogen means that the levels are lower than the amount of nitrogen present in the original biomass.

Present invention also provides a method which does not require application of pressure during extraction and consequently does not relate to solvents in the extraction process which have a low boiling point at normal pressure (1 atm). One example of a solvent with a low boiling temperature is propane which requires an external pressure in order to be kept in a liquid state at normal temperatures such as temperatures in the range of about 20° C. to about 100° C.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

A first aspect of the present invention provides a method for recovery of microbial lipids from oleaginous yeast biomass, said method comprising the steps of:
 (i) providing an aqueous suspension comprising fermentation broth containing oleaginous yeast biomass,
 (ii) subjecting said suspension to a hydrothermal treatment at a temperature of at least 160° C. for 1 second to 360 minutes at a pressure above 5 bar,
 (iii) subjecting the hydrothermally treated suspension to a separation step to obtain a liquid fraction and a yeast biomass fraction,
 (iv) subjecting the yeast biomass fraction to a drying step to obtain a dried yeast biomass fraction,
 (v) subjecting the dried biomass fraction to an extraction step with a liquid solvent to produce a liquid fraction comprising microbial lipids and a solid fraction comprising residual yeast biomass fraction,
 (vi) recovering the microbial lipids from the liquid fraction of step (v)
 (vii) optionally, isolating the residual biomass fraction from the product of step (v).

Consequently, in one aspect of present invention, the obtained liquid fraction in step (iii) is not extracted with a solvent to obtain any oil.

Another aspect of the present invention relates to a method for production of microbial lipids, the method comprising
 (a) providing a cultivation medium
 (b) providing a fermentation broth by inoculating the cultivation medium with an oleaginous yeast to produce oleaginous yeast biomass,
 (c) incubating said medium inoculated with said oleaginous yeast allowing lipid to accumulate
 (d) recovering microbial lipids from said oleaginous yeast biomass by the method for recovery of microbial lipids from oleaginous yeast biomass described herein.

Thus, one embodiment of the present invention relates to a method for production of microbial lipids, the method comprising
 (a) providing a cultivation medium
 (b) providing a fermentation broth by inoculating the cultivation medium with an oleaginous yeast to produce oleaginous yeast biomass,
 (c) incubating said medium inoculated with said oleaginous yeast allowing lipid to accumulate
 (i) providing an aqueous suspension comprising the fermentation broth containing oleaginous yeast biomass of step (c),
 (ii) subjecting said suspension to a hydrothermal treatment at a temperature of at least 160° C. for 1 second to 360 minutes at a pressure above 5 bar,
 (iii) subjecting the hydrothermally treated suspension to a separation step to obtain a liquid fraction and a yeast biomass fraction,
 (iv) subjecting the yeast biomass fraction to a drying step to obtain a dried yeast biomass fraction,
 (v) subjecting the dried biomass fraction to an extraction step with a liquid solvent to produce a liquid fraction comprising microbial lipids and a solid fraction comprising residual yeast biomass fraction,
 (vi) recovering the microbial lipids from the liquid fraction of step (v)
 (vii) optionally, isolating the residual biomass fraction from the product of step (v).

In a further embodiment, nutrients comprised in the liquid fraction obtained from the separation step (iii) are recycled to the cultivation medium (a).

A further aspect of the present invention provides the residual biomass obtainable with the methods according to the present invention.

In yet a further aspect of present invention, the obtained liquid fraction in step (iii) is not extracted with a solvent.

The inventors of present invention has also found that it is advantageous to wash the separated yeast biomass fraction in step (iii) with water prior to the drying in step (iv) and/or the extraction in step (v). This will result in a higher purity of the extracted oils with little or no need for further purification prior to subsequent reactions of the oils into e.g. fuel products.

The inventors have surprisingly found out that the problems related to harvesting of oleaginous yeast biomass having high lipids content can be solved by subjecting an aqueous suspension comprising oleaginous yeast biomass to a hydrothermal treatment (HTT) at a temperature of above 160° C. During the hydrothermal treatment, the density of the yeast biomass is decreased and the cells are combined together forming flocks, which enables efficient separation of liquid fraction by conventional filtration or centrifugation methods. Without being bound to any theory, it is considered that as a result of thermal treatment, the intracellular molecules of the yeast are extracted to water phase, which increases the oil share and decreases the density of biomass. It is also suggested that the hydrothermal treatment changes the surface structure and surface charge of yeast cells, which leads to formation of cell flocks enabling separation by filtration.

It was also found that the suitable heat treatment conditions (temperature and treatment time as variables) can be expressed using the severity factor used to simulate the extraction of carbohydrates from lignocellulosic biomasses. Severity factor log $R_0$ can be calculated using the formula (1) (Pedersen, M. and A. S. Meyer (2010). Lignocellulose pretreatment severity—relating pH to biomatrix opening. New Biotechnology 27(6): 739-750.).

The hydrothermal treatment (step (ii)) is conducted at a pressure above 5 bar, such as in the range of 6 to 25 bar, for example in the range of 10 to 25 bar, such as in the range of 10 to 15 bar. Alternatively, the pressure during hydrothermal treatment may be e.g. in the range of about 6.0 bar to about 20.0 bar, such as e.g. about 6.0 bar to about 7.0 bar, such as e.g. about 10.0 bar to about 11.0 bar, such as e.g. about 13.0 bar to about 18 bar, such as e.g. about 16 bar to about 19 bar.

Consequently, the above mentioned pressures may e.g. be distributed according to when the reaction temperature is about 160° C., the pressure may be e.g. about 6.2 bar to about 6.8 bar, or when the temperature is about 180° C., the pressure may be e.g. about 10.3 bar to about 11.0 bar, or when the temperature is about 190° C., the pressure may be e.g. about 13.7 bar to about 18 bar, or when the temperature is about 200° C., the pressure may be e.g. about 16.2 bar, or when the temperature is about 210° C., the pressure may be e.g. about 19.6 bar.

The hydrothermal processing (step (ii)) is conducted for 1 second to 360 minutes, such as in the range of 5 minutes to 240 min, for example in the range of 10 minutes to 120 min.

In one embodiment, the hydrothermal treatment (step (ii)) is conducted at a temperature in the range of 160 to 180° C. for 30 min to 180 min, such as 160° C. for 180 min or 180° C. for 30 to 60 min.

Thus, in one embodiment of the present invention, the hydrothermal treatment is conducted under conditions corresponding to a severity factor Log $R_0$ of at least about 3.5, preferably of at least about 3.9. In a further embodiment, the severity factor is in the range of about 3.5 to about 5.5 such as e.g. about 4 to about 4.5. The thermal treatment is typically conducted in a closed vessel.

The inventors have also surprisingly found that the lipids recovered by a method comprising hydrothermal treatment of yeast biomass at a temperature of above 160° C. and subsequent solvent extraction contains very small amounts of phosphorus and metal impurities. The hydrothermal treatment was found to enable effective harvesting of high lipid content microorganisms cells and recovery of high quality microbial oil with high yield.

Consequently, present invention relates to a method wherein the yield of the extracted oils or lipids is in the range of at least about 70%, such as e.g. about at least 80%, such as e.g. about at least 90%, such as e.g. about at least 95%, such as e.g. about at least 98%, such as e.g. about 100% based on the content of the oils or lipids present in the biomass.

The inventors have discovered the method of the present invention allows the efficient harvesting of oleaginous yeast biomass having a high content of microbial lipid (such as a lipid content of more than 35%) without major loss of microbial lipid.

In one embodiment of the present invention, the yeast biomass has a lipid content of at least 20% by weight of cell mass. In a preferred embodiment, the yeast biomass has a lipid content of at least 30% by weight of cell mass. In an even more preferred embodiment, the yeast biomass has a lipid content of at least 35% by weight of cell mass, such as e.g. at least about 40% on a dry weight basis, or such as e.g. at least about 50% on a dry weight basis, such as e.g. at least about 60% on a dry weight basis, such as e.g. at least about 70% on a dry weight basis, such as e.g. at least about 80% on a dry weight basis.

The extraction of lipids can be performed using any traditional solvent like ethanol or hydrocarbons. Extraction using hexane is preferred as this ensures good extraction yield and oil quality. The extraction step can be conducted with conventional means. In one embodiment of the present invention, the extraction step (v) is conducted using a hydrocarbon solvent such as a hydrocarbon solvent comprising lower alkanes, preferably aliphatic $C_2$-$C_8$ alkanes. Even more preferred is $C_5$-$C_8$ alkanes, such as e.g. pentanes, hexanes, heptanes or octanes.

Furthermore the inventors surprisingly found out that in case the aqueous suspension comprises fermentation broth obtained from cultivation of oleaginous yeasts in a cultivation medium comprising lignocellulose hydrolysate, the hydrothermal treatment increases the amount of residual biomass. This indicates that the dissolved lignocellulosic material present in the fermentation broth is transformed into solid state during the hydrothermal treatment and separated with residual biomass in the subsequent separation step. The recovery of dissolved lignocellulosic material from the aqueous suspension to the solid biomass fraction has the advantage of increasing the amount of valuable residual biomass fraction obtained from the recovery process. Simultaneously, this reduces the chemical oxygen demand of the wastewater fraction obtained from oleaginous yeast production using lignocellulosic material or hydrolysate.

In a preferred embodiment of the present invention, the fermentation broth is obtained from cultivation of oleaginous yeasts in a cultivation medium comprising lignocellulosic material. In another preferred embodiment, the fermentation broth is obtained from cultivation of oleaginous yeasts in a cultivation medium comprising lignocellulose hydrolysate.

The advantages of the present invention include that the hydrothermal treatment enables efficient harvesting of oleaginous yeast biomass having high lipid content from aqueous suspensions with conventional harvesting means such as filtration and centrifugation. Efficient harvesting means that the harvested biomass has high dry matter content and that no oil or oil containing cells are lost during the harvesting process. As a result, only a small amount of water has to be removed by drying before the subsequent extraction step and oil is not lost during the processing.

The present invention thus enables economically feasible recovery of lipids from oleaginous yeast biomass having high lipid content since the hydrothermal treatment minimizes the need for drying, which is known to be the most energy intensive step of the recovery process.

The oleaginous yeast may be any yeast capable of accumulating intercellular lipids such that the lipids mounts at least 15% (w/w) of the total biomass (per cell dry weight) of the yeast when it is cultivated under suitable conditions. The oleaginous yeast includes oleaginous yeast species of the genera *Clavispora, Geotrichum, Deparyomyces, Pachysolen, Kluyveromyces, Galactomyces, Hansenula, Leucosporidium, Saccharomyces, Sporobolomyces, Sporidiobolus, Waltomyces, Endomycopsis, Cryptococcus*, such as *Cryptococcus curvatus, Rhodosporidium*, such as *Rhodosporidium toruloides* or *Rhodosporidium fluviale, Rhodotorula*, such as *Rhodotorula glutinis, Yarrowia*, such as *Yarrowia lipolytica, Pichia*, such as *Pichia stipitis, Candida* such as *Candida curvata, Lipomyces* such as *Lipomyces starkeyi* and *Trichosporon* such as *Trichosporon cutaneum* or *Trichosporon pullulans*.

Preferably the yeast strains are those belonging to *Candida, Rhodotorula, Trichosporon, Rhodosporidium, Lipomyces Cryptococcus* or *Saccharomyces*. In a preferred embodiment of the present invention, the yeast is a yeast of the genus *Rhodosporidium, Rhodotorula, Lipomyces Cryptococcus* or *Saccharomyces*. In a further embodiment oleaginous yeast used by the method of the present invention is a mixture of two or more species of oleaginous yeasts.

The hydrothermal treatment at a temperature higher than 160° C. also disrupts the yeast cells and enables efficient extraction of lipids without separate cell disruption step. The oil extracted from hydrothermally treated yeast biomass was found to contain low amounts of phosphorus and metal impurities, which is essential for the subsequent processing of lipids to fuel components and which reduces the need for further purification steps for the raw microbial oil.

Lignocellulosic Material

The terms "lignocellulosic biomass" or "lignocellulosic material" is meant to include but is not limited to woody plants or non-woody, herbaceous plants or other materials containing cellulose and/or hemi-cellulose: Materials can be agricultural residues (such as wheat straw, rice straw, chaff, hulls, corn stover, sugarcane bagasse, sugar cane tops and leaves), dedicated energy crops (such as switchgrass, *Miscanthus, Arundo donax*, reed canary grass, willow, water hyacinth, energy cane, energy sorghum), wood materials or residues (including sawmill and pulp and/or paper mill residues or fractions, such as hemicellulose, spent sulphite liquor, waste fibre and/or primary sludge), moss or peat, or municipal paper waste. The term lignocellulosic material comprises also low lignin materials, materials such as macroalgae biomass. In addition, the materials comprise also hemicellulose or cellulose fractions from industrial practises. The term lignocellulosic material encompasses any kind of cellulose fraction. The raw materials or certain fractions, such as hemicellulose and/or cellulose, of raw materials from different origin, plant species, or industrial processes can be mixed together and used as raw materials for cultivating microorganism biomass according to this disclosure. Typically the lignin content in lignocellulose is higher than 5%. Lignocellulosic biomass may also contain starch, e.g. in the case of whole plants.

The term lignocellulosic material comprises at least 50 wt % lignocellulose, preferably at least 60 wt % lignocellulose, more preferably at least 70 wt % lignocellulose, most preferably at least 80 wt % lignocellulose. Usually lignocellulosic material comprises 60-95 wt % lignocellulose, typically 70-90 wt %, or 80-90 wt % lignocellulose.

Cultivation Medium Comprising Lignocellulosic Material

"A cultivation medium comprising lignocellulosic material" means a cultivation medium for cultivating a microorganism, which medium comprises lignocellulose, fragments of lignocellulose or hydrolysis products of lignocellulose including nitrogen compounds originating from proteins and metals, and other components necessary for cultivating said microorganism, such as a source of nitrogen, phosphorus, inorganic salts and/or trace elements, de-foaming agents. Lignocellulose may function as a carbon source for said microorganism, but it may also have other functions in the cultivation medium.

Hydrolysis

"Hydrolysis" refers here to saccharification of polymeric sugars to sugar oligomers and monomers. Saccharification is typically carried out in two phases: first the substrate i.e. lignocellulosic material or lignocellulose is hydrolyzed by thermochemical or chemical methods and then by using enzymes capable of hydrolysing polymeric sugars. Alternatively and depending on the lignocellulosic material, saccharification can be carried out by using thermochemical or chemical methods or by enzymes capable of hydrolysing polymeric sugars or some combination of these methods. Chemical methods include, but are not limited to acid treatment.

Hydrolysate

The terms "hydrolysate" or "hydrolysed material" refers here to material that has undergone hydrolysis.

Lignocellulose Hydrolysate

The term "lignocellulose hydrolysate" refers here to hydrolysis products of lignocellulose or lignocellulosic material comprising cellulose and/or hemicellulose, oligosaccharides, mono- and/or disaccharides, acetic acid, formic acid, other organic acids, furfural, hydroxymethyl furfural, levulinic acid, phenolic compounds, other hydrolysis and/or degradation products formed from lignin, cellulose, hemicellulose and/or other components of lignocellulose, nitrogen compounds originating from proteins, metals and/or non-hydrolyzed or partly hydrolyzed fragments of lignocellulose.

Hydrothermal Treatment

"Hydrothermal treatment" or "hydrothermal processing" are used here synonymously and refer to a process in which an aqueous suspension comprising microbial biomass is heated to a temperature of at least 160° C. and subjecting the aqueous suspension comprising said microbial biomass to a temperature of at least 160° C. for Is to 360 minutes at a pressure above 5 bar.

It should be notes that in the context of the present invention the above mentioned methods, i.e. thermochemical treatment, steam explosion, hot water extraction, autohydrolysis, sub critical water treatment, super critical water treatment, strong acid treatment, mild acid treatment, alkaline treatment (e.g. lime, ammonia), Organosolv treatment (e.g. alcohols, organic acids), mechanical treatment, thermomechanical treatment and ionic liquid treatment does not fall within the definition of hydrothermal processing (or hydrothermal treatment, heat treatment, HTT).

Severity Factor

The term "severity factor" refers here to a parameter Log $R_0$, which is calculated based on the following equation and which describes the hydrothermal conditions in terms of temperature and time.

$$R_0 = \int_a^b \exp\left(\frac{T(t)-100}{14.75}\right) dt = t \cdot \exp\left(\frac{T(t)-100}{14.75}\right) \quad \text{Formula (1)}$$

where $R_0$ is the severity factor, $T(t)$ is the treatment temperature in ° C. and t is the treatment time in minutes.

Oleaginous Microorganism

The term "oleaginous microorganism" refers to a lipid-producing microorganism. Thus, oleaginous yeast refers to is a lipid-producing microorganism. When a lipid-producing microorganism has been used for single cell oil production, the microbial biomass is residual biomass from a single cell oil production process.

The oleaginous yeast referred to herein and used by the present can readily accumulate lipids or have been genetically modified to accumulate lipids or to improve accumulation of lipids. Preferably the oleaginous yeast is capable of utilizing C6 and C5 sugars are used.

In the context of the present invention, the oleaginous yeast refers to a yeast which is capable of accumulating intercellular lipids such that the lipids amounts at least 15% (w/w) of the total biomass (per cell dry weight) of the yeast when it is cultivated under suitable conditions. In a preferred embodiment, the oleaginous microbe is capable of accumulating at least 20% (w/w) of the total biomass of the microbe (per cell dry weight). In an even more preferred embodiment, the oleaginous yeast is capable of accumulating at least 35% (w/w) of the total biomass of the yeast (per cell dry weight). In yet a further preferred embodiment the oleaginous yeast is capable of accumulating at least about 40% (w/w) on a dry weight basis, or such as e.g. at least about 50% (w/w) on a dry weight basis, such as e.g. at least about 60% (w/w) on a dry weight basis, such as e.g. at least about 70% (w/w) on a dry weight basis, such as e.g. at least about 80% (w/w) on a dry weight of lipids of the total biomass (per cell dry weight).

Microbial Lipid or Lipid

In the context of the present invention "microbial lipid", "lipid" or "intracellular lipid" or "oil product" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as tri-acylglycerols, diacylglycerols, or monoacylglycerols. Preferred lipids in the present invention are fats, oils, waxes, acylglycerols and fatty acids and their derivatives, in particular triacylglycerols and wax esters. In the context of the present invention the lipids are synthesized by and accumulated in microbes (intracellular lipids). In another embodiment of the invention, lipids are synthetized by and excreted by microbes (extracellular lipids).

In connection of this invention single cell oil is used as synonym for lipids and fat.

The term "acyglycerol" refers to an ester of glycerol and fatty acids. Acylglycerols occur naturally as fats and fatty oils. Examples of acylglycerols include triacylglycerols (TAGs, triglycerides), diacylglyc-erols (diglycerides) and monoacylglycerols (monoglycerides).

Biomass

In the context of the present invention the term "biomass" (or "cell mass") refers to biological material derived from living or non-living organisms. "Yeast biomass" thus refers to biomass derived from yeast. The microbial biomass may be obtained from a single species of yeast or a pool of different species of yeast. The yeast biomass may exist in a living or a non-living state. In the context of the present invention, the yeast biomass, which has been subjected to hydrothermal heat treatment (HTT) is in a non-living state.

Residual Cell Mass

In the context of the present invention "residual cell mass" or "residual biomass fraction" refers to a solid, semi-solid or flowing material fraction, which contains microorganisms from which the intracellular lipids have been recovered.

Dry Matter

"DM" or "dry weight" refers here to dry matter and is a measurement of the mass of a material when it has been subjected to a treatment that essentially removes water from the material (i.e. material is completely dried).

Hydrothermal Treatment of the Aqueous Suspension Comprising Microbial Biomass and Subsequent Processing The aqueous suspension comprising biomass can be hydrothermally processed as such coming from the cultivation or the suspension can be first concentrated. It is also possible to adjust the pH of the suspension at this point. More acidic pH enables greater dissolution of solid material leading to flotation with some yeast in lower temperatures than in higher pH. Though, the pH adjustment does not affect the severity factor needed to make these yeasts filterable. In one embodiment of the invention, the pH value of the aqueous suspension in step (i) is below 6, preferably below 5. However, in another aspect of the invention, no external acidification is needed such that an acidic component is added in order to adjust or regulate the pH of the reaction mixture.

The hydrothermal processing of the biomass suspension can be conducted with direct or indirect heating. In direct heating the suspension can be heated with steam. In indirect heating the suspension may be heated through a wall of a vessel containing the suspension or circulating the suspension through tubes or shells of a heat exchanger. The heating can be done in a closed continuous or a batch system.

The aqueous suspension typically has a dry matter content of at least 3%, preferably of at least 10% such as 15 to 35%.

After the hydrothermal processing the solid material containing the oil can be separated from the liquid by methods such as centrifugation or filtration. In one embodiment of the present invention, the separation step (iii) is performed by centrifugation or involves a step of centrifugation. In another embodiment, the separation step (iii) is performed by filtration or involves a step of filtration.

Filtration is preferred as with using filter press as a high dry matter content of the solid material up to 70% is obtainable. In one embodiment of the present invention, the yeast biomass fraction obtained from the separation step (iii) has a dry matter content of at least 50%, such as at least 60%. In a preferred embodiment, the yeast biomass fraction obtained from the separation step (iii) has a dry matter content of at least 65%. In another preferred embodiment, the yeast biomass fraction obtained from the separation step (iii) has a dry matter content of at least 70%.

The harvested wet biomass can be washed using water to further reduce the impurities of the extracted oil (cf. Example 9). Thus in one embodiment, the yeast biomass fraction obtained from the hydrothermal treatment step is subjected to water washing step prior to the extraction step (v).

Before the extraction using hydrocarbon solvent, most preferably hexane, the solid material is dried to a dry matter content of >90%. In one embodiment of the present invention, the dried biomass fraction (of step (iv)) has a dry matter content of at least 90%, preferably of at least 95%.

Any known drying technology can be used, but the choice can affect the quality of the extracted oil (cf. Example 9). It has been found that the amount of impurities in the extracted microbial oil, especially the amount of nitrogen can be adjusted by optimizing the drying of the biomass before the oil extraction step. In one embodiment of the present invention, the drying step (iv) is conducted at a temperature of below 100° C., preferably below 90° C. In one embodiment of the present invention, the extraction step (v) is conducted at a temperature of below 90° C., preferably below 50° C. In another embodiment, the drying step (iv) is conducted in vacuum and at a temperature of the biomass of below 90° C., preferably below 70° C. In a further embodiment, the extraction step (v) is conducted at a temperature of below 90° C., preferably below 70° C.

In one embodiment of the present invention, the extraction step (v) is conducted using a hydrocarbon solvent such as a hydrocarbon solvent comprising lower alkanes, preferably aliphatic $C_2$-$C_8$ alkanes.

The extraction step can be done using any known extraction technology. The extraction process produces the raw microbial oil and the oil extracted residual biomass, which needs to be desolventized before further usage.

Microbial Lipids Obtainable by the Method of the Present Invention.

As mentioned herein, the inventors have surprisingly discovered that the lipids recovered by a method comprising hydrothermal treatment of yeast biomass at a temperature of above 160° C. and subsequent solvent extraction contains very small amounts of phosphorus and metal impurities.

Accordingly, a further aspect of the present invention relates to microbial lipids obtainable by the method of the present invention.

The inventors have discovered that the amount of elemental phosphorous is reduced if the microbial lipids are obtained by the method of the present. Accordingly one embodiment of the present invention relates to microbial lipids obtainable by the method of the present invention, wherein the concentration of elemental phosphorous is not more than 20 mg/kg of microbial lipid, preferably not more than 10 mg/kg, even more preferably not more than 5 mg/kg, most preferably not more than 1 mg elemental phosphorus/kg of microbial lipids.

The inventors have further discovered that the amount of elemental nitrogen is reduced if the microbial lipids are obtained by the method of the present. Accordingly one embodiment of the present invention relates to microbial lipids obtainable by the method of the present invention, wherein the concentration of elemental nitrogen is not more than 600 mg elemental nitrogen/kg of microbial lipids, more preferably not more than 200 mg/kg, most preferably not more than 100 mg elemental nitrogen/kg of microbial lipids.

In a further embodiment, the concentration elemental iron, sodium, silica, calcium, magnesium, manganese or potassium in the microbial oil is not more than 20 mg/kg, preferably not more than 10 mg/kg, even more preferably not more than 5 mg/kg, most preferably not more than 1 mg/kg. For examples, the concentration elemental iron in the microbial oil is not more than 20 mg/kg, preferably not more than 10 mg/kg, even more preferably not more than 5 mg/kg, most preferably not more than 1 mg/kg. For examples, the concentration elemental sodium in the microbial oil is not more than 20 mg/kg, preferably not more than 10 mg/kg, even more preferably not more than 5 mg/kg, most preferably not more than 1 mg/kg. For examples, the concentration elemental silica in the microbial oil is not more than 20 mg/kg, preferably not more than 10 mg/kg, even more preferably not more than 5 mg/kg, most preferably not more than 1 mg/kg. For examples, the concentration elemental calcium in the microbial oil is not more than 20 mg/kg, preferably not more than 10 mg/kg, even more preferably not more than 5 mg/kg, most preferably not more than 1 mg/kg. For examples, the concentration elemental magnesium in the microbial oil is not more than 20 mg/kg, preferably not more than 10 mg/kg, even more preferably not more than 5 mg/kg, most preferably not more than 1 mg/kg. For examples, the concentration elemental manganese in the microbial oil is not more than 20 mg/kg, preferably not more than 10 mg/kg, even more preferably not more than 5 mg/kg, most preferably not more than 1 mg/kg. For examples, the concentration elemental potassium in the microbial oil is not more than 20 mg/kg, preferably not more than 10 mg/kg, even more preferably not more than 5 mg/kg, most preferably not more than 1 mg/kg.

Yet a further aspect relates to a microbial oil product. In embodiment of the present invention the concentration of elemental phosphorous in microbial oil product is not more than 20 mg/kg of microbial lipid, preferably not more than 10 mg/kg, even more preferably not more than 5 mg/kg, most preferably not more than 1 mg elemental phosphorus/kg of microbial oil product.

In a second embodiment of the present invention the concentration of elemental nitrogen in microbial oil product is not more than 600 mg elemental nitrogen/kg of microbial lipids, more preferably not more than 200 mg/kg, most preferably not more than 100 mg elemental nitrogen/kg of microbial oil product.

In a further embodiment, the concentration elemental iron, sodium, silica, calcium, magnesium, manganese or potassium in the microbial oil product is not more than 20 mg/kg, preferably not more than 10 mg/kg, even more preferably not more than 5 mg/kg, most preferably not more than 1 mg/kg. For examples, the concentration elemental iron in the microbial oil product is not more than 20 mg/kg, preferably not more than 10 mg/kg, even more preferably not more than 5 mg/kg, most preferably not more than 1 mg/kg. For examples, the concentration elemental sodium in the microbial oil product is not more than 20 mg/kg, preferably not more than 10 mg/kg, even more preferably not more than 5 mg/kg, most preferably not more than 1 mg/kg. For examples, the concentration elemental silica in the microbial oil product is not more than 20 mg/kg, preferably not more than 10 mg/kg, even more preferably not more than 5 mg/kg, most preferably not more than 1 mg/kg. For examples, the concentration elemental calcium in the microbial oil product is not more than 20 mg/kg, preferably not more than 10 mg/kg, even more preferably not more than 5 mg/kg, most preferably not more than 1 mg/kg. For examples, the concentration elemental magnesium in the microbial oil product is not more than 20 mg/kg, preferably not more than 10 mg/kg, even more preferably not more than 5 mg/kg, most preferably not more than 1 mg/kg. For examples, the concentration elemental manganese in the microbial oil product is not more than 20 mg/kg, preferably not more than 10 mg/kg, even more preferably not more than 5 mg/kg, most preferably not more than 1 mg/kg. For examples, the concentration elemental potassium in the microbial oil product is not more than 20 mg/kg, preferably not more than 10 mg/kg, even more preferably not more than 5 mg/kg, most preferably not more than 1 mg/kg.

The invention is illustrated by the following non-limiting items.

Item 1. A method for recovery of microbial lipids from oleaginous yeast biomass, said method comprising the steps of:

(i) providing an aqueous suspension comprising fermentation broth containing oleaginous yeast biomass, (ii) subjecting said suspension to a hydrothermal treatment at a temperature of at least 160° C. for 1 second to 360 minutes at a pressure above 5 bar, (iii) subjecting the hydrothermally treated suspension to a separation step to obtain a liquid fraction and a yeast biomass fraction, (iv) subjecting the yeast biomass fraction to a drying step to obtain a dried yeast biomass fraction, (v) subjecting the dried biomass fraction to an extraction step with a liquid solvent to produce a liquid fraction comprising microbial lipids and a solid fraction comprising residual yeast biomass fraction, (vi) recovering the microbial lipids from the liquid fraction of step (v)

(vii) optionally, isolating the residual biomass fraction from the product of step (v).

Item 2. The method according to item 1 wherein the fermentation broth is obtained from cultivation of oleaginous yeasts in a cultivation medium comprising lignocellulosic material.

Item 3. The method according to item 1 wherein the fermentation broth is obtained from cultivation of oleaginous yeasts in a cultivation medium comprising lignocellulose hydrolysate.

Item 4. The method according to any of items 1-3 wherein the yeast biomass fraction obtained from the separation step has a dry matter content of at least 50%, preferably of at least 60%.

Item 5. The method according to any of items 1-4 wherein the dried biomass fraction has a dry matter content of at least 90%, preferably of at least 95%.

Item 6. The method according to any of items 1-5 wherein the thermal treatment is conducted in a closed vessel.

Item 7. The method according to any of items 1-6 wherein the hydrothermal treatment is conducted under conditions corresponding to a severity factor Log $R_0$ of at least 3.5, preferably of at least 3.9.

Item 8. The method according to any of items 1-7 wherein the yeast biomass has a lipid content of at least 20%, preferably of at least 30%, most preferably of at least 35% by weight of cell mass.

Item 9. The method according to any of items 1-8 wherein the yeast biomass fraction obtained from the hydrothermal treatment step is subjected to water washing step prior to the extraction step.

Item 10. The method according to any of items 1-9 wherein the aqueous suspension has a dry matter content of at least 3%, preferably of at least 10%.

Item 11. The method according to any of items 1-10 wherein the yeast is of genus *Rhodosporidium, Rhodotorula, Lipomyces, Cryptococcus* or *Saccharomyces*.

Item 12. The method according to any of the items 5-11 wherein liquid solvent is a hydrocarbon solvent comprising lower alkanes, preferably aliphatic $C_2$-$C_8$ alkanes.

Item 13. The method according to any of the preceding items, wherein the separation (iii) is performed by centrifugation or involves a step of centrifugation.

Item 14. The method according to any of the preceding items, wherein the separation (iii) is performed by filtration or involves a step of filtration.

Item 15. The method according to any of the preceding items, wherein the drying step (iv) is conducted in vacuum and at a temperature of the biomass of below 90° C., preferably below 70° C.

Item 16. The method according to any of the preceding items, wherein the extraction step (v) is conducted at a temperature of below 90° C., preferably below 70° C.

Item 17. The method according to any of the preceding items, wherein the pH value of the aqueous suspension in step (i) is below 6, preferably below 5.

Item 18. Residual biomass obtainable with the method according to any of the items 1-17.

Item 19. A method for production of microbial lipids, the method comprising (a) providing a cultivation medium (b) providing a fermentation broth by inoculating the cultivation medium with an oleaginous yeast to produce oleaginous yeast biomass, (c) incubating said medium inoculated with said oleaginous yeast allowing lipid to accumulate (d) recovering microbial lipids from said oleaginous yeast biomass with the method according to any of the items 1-18

Item 20. The method according to item 19 wherein nutrients comprised in the liquid fraction obtained from the separation step are recycled to the cultivation medium.

Item 21. Microbial lipids obtainable by the method according to any of the items 1-20

Item 22. A microbial oil product, wherein the oil is containing not more than 20 mg/kg of elemental phosphorus, preferably not more than 10 mg/kg, even more preferably not more than 5 mg/kg, most preferably not more than 1 mg/kg of elemental phosphorus.

Item 23. A microbial oil product according to item 22, wherein the oil contains not more than 600 mg/kg of elemental nitrogen, more preferably not more than 200, most preferably not more than 100 mg/kg of elemental nitrogen.

Item 24. A microbial oil product according to item 22 or 23 wherein the oil contains not more than 20 mg/kg, preferably not more than 10 mg/kg, even more preferably not more than 5 mg/kg, most preferably not more than 1 mg/kg of any of elemental iron, sodium, silica, calcium, magnesium, manganese or potassium.

Present invention also relates to specific embodiments in accordance to the following Articles:

Articles

1. A method for recovery of microbial lipids from oleaginous yeast biomass, said method comprising the steps of:

(i) providing an aqueous suspension comprising fermentation broth containing oleaginous yeast biomass, (ii) subjecting said suspension to a hydrothermal treatment at a temperature of at least 160° C. for 1 second to 360 minutes at a pressure above 5 bar, (iii) subjecting the hydrothermally treated suspension to a separation step to obtain a liquid fraction and a yeast biomass fraction, (iv) subjecting the yeast biomass fraction to a drying step to obtain a dried yeast biomass fraction, (v) subjecting the dried biomass fraction to an extraction step with a liquid solvent to produce a liquid fraction comprising microbial lipids and a solid fraction comprising residual yeast biomass fraction, (vi) recovering the microbial lipids from the liquid fraction of step (v)

(vii) optionally, isolating the residual biomass fraction from the product of step (v).

2. The method according to article 1 wherein the fermentation broth is obtained from cultivation of oleaginous yeasts in a cultivation medium comprising lignocellulose hydrolysate.

3. The method according to any of articles 1 or 2 wherein the yeast biomass fraction obtained from the separation step has a dry matter content of at least 50%, preferably of at least 60%.

4. The method according to any of articles 1-3 wherein the dried biomass fraction has a dry matter content of at least 90%, preferably of at least 95%.

5. The method according to any of articles 1-4 wherein the hydrothermal treatment is conducted under conditions corresponding to a severity factor Log $R_0$ of at least 3.5, preferably of at least 3.9.

6. The method according to any of articles 1-5 wherein the yeast biomass has a lipid content of at least 20%, preferably of at least 30%, most preferably of at least 35% by weight of cell mass.

7. The method according to any of articles 1-6 wherein the aqueous suspension has a dry matter content of at least 3%, preferably of at least 10%.

8. The method according to any of articles 1-7 wherein the yeast is of genus *Rhodosporidium, Rhodotorula, Lipomyces, Cryptococcus* or *Saccharomyces*.

9. The method according to any of the preceding articles, wherein the separation (iii) is performed by centrifugation or involves a step of centrifugation.

10. The method according to any of the preceding articles, wherein the separation (iii) is performed by filtration or involves a step of filtration.

11. The method according to any of the preceding articles, wherein the drying step (iv) is conducted in vacuum and at a temperature of the biomass of below 90° C., preferably below 70° C.

12. The method according to any of the preceding articles, wherein the extraction step (v) is conducted at a temperature of below 90° C., preferably below 70° C.

13. The method according to any of the preceding articles, wherein the pH value of the aqueous suspension in step (i) is below 6, preferably below 5.

14. Residual biomass obtainable with the method according to any of the articles 1-13.

15. Microbial lipids obtainable by the method according to any of the articles 1-13

16. A microbial oil product containing not more than 20 mg/kg of elemental phosphorus, preferably not more than 10 mg/kg, even more preferably not more than 5 mg/kg, most preferably not more than 1 mg/kg of elemental phosphorus.

17. A microbial oil product according to article 16 wherein the oil contains not more than 600 mg/kg of elemental nitrogen, more preferably not more than 200, most preferably not more than 100 mg/kg of elemental nitrogen.

18. A microbial oil product according to article 16 or 17 wherein the oil contains not more than 20 mg/kg, preferably not more than 10 mg/kg, even more preferably not more than 5 mg/kg, most preferably not more than 1 mg/kg of any of elemental iron, sodium, silica, calcium, magnesium, manganese or potassium.

EXAMPLES

The invention is illustrated by the following non-limiting examples. The invention can be applied to other microorganisms than those illustrated in examples. It should be understood that the embodiments given in the description above and in the examples are for illustrative purposes only, and that various changes and modifications are possible within the scope of invention.

Example 1

Cultivation of *Rhodosporidium* Biomass on Pure Sugars for Thermal Harvesting Experiments

*Rhodosporidium toruloides* strain CBS 8587 (or other *R. toruloides* strain, which are readily available from recognized microbial culture collections) was grown under aeration in a pilot fermentor. Fermentation was done as fed-batch fermentation using glucose as carbon source. After 24 h batch phase glucose syrup was added to the fermentor periodically during the 143 h cultivation. Growth medium was supplemented with yeast extract (8 g/l), (NH4)2SO4 (3 g/l), MgCl2 (2 g/l), K2HPO4 (9 g/l) and CaCl2 (0.4 g/l) and trace minerals ZnSO4 (0.0003 g/l), CuCl (0.0002 g/l) and MnCl2 (0.03 g/l). In the end of the cultivation the oil content of the biomass was 46.8% of the dry weight of the cell. The resulting biomass suspension was pasteurized and used in the thermal harvesting tests in the following examples.

Example 2

Cultivation of *Rhodosporidium* Biomass on Lignocellulosic Sugars for Thermal Harvesting Experiments
Batch Number 1:

*Rhodosporidium toruloides* strain CBS 8587 (or other *R. toruloides* strain, which are readily available from recognized microbial culture collections) was grown under aeration in a pilot fermentor. Fermentation was done as fed-batch fermentation using lignocellulosic hydrolysate syrup as the carbon source. After 12 h batch fermentation lignocellulose hydrolysate syrup was added to the fermentor periodically during the 144 h cultivation. Growth medium was supplemented with yeast extract (17 g/l), (NH4)2SO4 (2.1 g/l), (NH4)2HPO4 (2.1 g/l) MgCl2 (3.3 g/l), K2HPO4 (5 g/l) and CaCl2 (0.2 g/l) and trace minerals ZnSO4 (0.0005 g/l), CuCl (0.0003 g/l) and MnCl2 (0.05 g/l). In the end of the cultivation the oil content of the biomass was 34.6% of the dry weight of the cell. The resulting biomass suspension was pasteurized and used in the thermal harvesting tests in the following examples.
Batch Number 2:

*Rhodosporidium toruloides* strain CBS 8761 (or other *R. toruloides* strain, which are readily available from recognized microbial culture collections) was grown under aeration in a pilot fermentor. Fermentation was done as fed-batch fermentation using lignocellulosic hydrolysate syrup as the carbon source. Lignocellulose hydrolysate syrup was added to the fermenter periodically throughout the 154 h cultivation. Growth medium was supplemented with yeast extract (8.3 g/l), (NH4)2SO4 (1.3 g/l), (NH4)2HPO4 (2.0 g/l), MgCl2 (1.7 g/l), KH2PO4 (1.8 g/l) and trace minerals ZnSO4 (0.0005 g/l), CuCl2 (0.0003 g/l) and MnCl2 (0.05 g/l), Na2MoO4 (0.0003 g/l). In the end of the cultivation the oil content of the biomass was 47.7% of the dry weight of the cell. The resulting biomass suspension was pasteurized and used in the thermal harvesting tests in the following examples.

Example 3

Cultivation of *Cryptococcus* Biomass on Pure Sugar for Thermal Harvesting Experiments
Three *Cryptococcus* biomass batches were used in the thermal harvesting tests.
Batch Number 1:

*Cryptococcus curvatus* strain CBS 5324 (or other *C. curvatus* strain, which are readily available from recognized microbial culture collections) was grown under aeration in a pilot fermentor. Fermentation was done as fed-batch fermentation using glucose as carbon source. Glucose syrup was added to the fermentor periodically throughout the 119 h cultivation. Growth medium was supplemented with yeast extract (10 g/l), malt extract (3 g/l), (NH4)2SO4 (1.5 g/l), (NH4)2HPO4 (1.5 g/l), MgCl2 (1.8 g/l), KH2PO4 (3 g/l), K2HPO4 (1 g/l) and CaCl2 (0.4 g/l) and trace minerals ZnSO4 (0.0003 g/l), CuCl (0.0002 g/i) and MnCl2 (0.03 g/l). In the end of the cultivation the oil content of the biomass was 38.5% of the dry weight of the cell. The resulting biomass suspension was pasteurized and used in the thermal harvesting tests in the following examples.

Batch Number 2:

*Cryptococcus curvatus* strain CBS 5324 TKK mutant 40 (or other *C. curvatus* strain, which are readily available from recognized microbial culture collections) was grown under aeration in a pilot fermentor. Fermentation was done as fed-batch fermentation using glucose as carbon source. Glucose syrup was added to the fermentor periodically throughout the 114 h cultivation. Growth medium was supplemented with yeast extract (6 g/l), (NH4)2SO4 (1.8 g/l), (NH4)2HPO4 (1.8 g/l), MgCl2 (1.8 g/l), KH2PO4 (3 g/l) and CaCl2 (0.3 g/l) and trace minerals ZnSO4 (0.0003 g/l), CuCl (0.0002 g/l) and MnCl2 (0.03 g/l). In the end of the cultivation the oil content of the biomass was 47.9% of the dry weight of the cell. The resulting biomass suspension was pasteurized and used in the thermal harvesting tests in the following examples.

Batch Number 3:

*Cryptococcus curvatus* strain CBS 5324 TKK mutant 40 (or other *C. curvatus* strain, which are readily available from recognized microbial culture collections) was grown under aeration in a pilot fermentor. Fermentation was done as fed-batch fermentation using glucose as carbon source. Glucose syrup was added to the fermentor periodically throughout the 90 h cultivation. Growth medium was supplemented with yeast extract (6 g/l), (NH4)2SO4 (1.8 g/l), (NH4)2HPO4 (1.8 g/l), MgCl2 (1.8 g/l), KH2PO4 (3 g/l) and CaCl2 (0.3 g/l) and trace minerals ZnSO4 (0.0003 g/l), CuCl (0.0002 g/l) and MnCl2 (0.03 g/l). In the end of the cultivation the oil content of the biomass was 40.3% of the dry weight of the cell. The resulting biomass suspension was pasteurized and used in the thermal harvesting tests in the following examples.

Example 4

Effect of Hydrothermal Treatment on Filterability of the Yeast Biomasses

Heat treatment conditions (temperature and treatment time as variables) is expressed using the severity factor used to simulate the extraction of carbohydrates from lignocellulosic biomasses. Severity factor Log $R_0$ is calculated using the formula (1) (Pedersen and Meyer, 2010).

Aqueous yeast suspensions were treated at different severity in a 1 liter pressure reactor (Parr Instruments). The reactor was heated under stirring (500 rpm) and samples were withdrawn at certain severity Log $R_0$ values. Filterability of the withdrawn samples was tested with a 2 um filter. The effect of HTT to filterability of the yeast biomass suspensions is shown in Tables 1-3.

TABLE 1

Filterability of *Rhodosporidium* yeast biomass of Example 1
Solids DW 5.93 wt %, pH 5.75

| HTT temperature | Biomass filterable at | Log$R_0$ when biomass filterable |
|---|---|---|
| Heating to 160° C. | 90 min at 160° C. | 3.75 |
| Heating to 180° C. | 30 min at 180° C. | 3.9 |
| Heating to 200° C. | 0 min at 200° C. | 3.8 |

TABLE 2

Filterability of *Rhodosporidium* yeast biomass of batch 1 of Example 2
Solids DW 3.8 wt %, pH 5.9

| HTT temperature | Biomass filterable at | Log$R_0$ when biomass filterable |
|---|---|---|
| Heating to 180° C. | 30 min at 180° C. | 3.9 |
| Heating to 190° C. | 10 min at 190° C. | 3.9 |

TABLE 3

Filterability of *Cryptococcus* yeast biomass of Example 3, batch 1
Solids DW 7.09 wt %, pH 5.5

| HTT temperature | Biomass filterable at | Log$R_0$ when biomass filterable |
|---|---|---|
| Heating to 160° C. | 150 min at 160° C. | 4.0 |
| Heating to 180° C. | 60 min at 180° C. | 4.2 |

Based on the results of the example 4, the required severity factor of the hydrothermal treatment (HTT) to make the aqueous suspension containing yeast biomass filterable depends on the yeast genus and to some extent on the pH value of the aqueous suspension. Generally a severity factor of Log $R_0 > 3.9$ of the HTT is required to make the aqueous suspension containing yeast biomass filterable.

Example 5

Effect of Hydrothermal Treatment on Extraction Yield of Microbial Oil

*Rhodosporidium* yeast suspension of Example 1 was subjected to different hydrothermal treatments to study the effect of HTT severity to extraction yield of lipids.

First the pasteurized (80° C., 15 min) biomass suspension was centrifuged with Sorvall centrifuge at 10 000 rpm/20 min to obtain a suspension with solids dry matter content of 25%. The resulting solid material was dried to 98% solids dry matter content thus creating a yeast biomass harvested without using hydrothermal treatment. This biomass is named "no HTT" in Table 4 of this example.

Additionally yeast suspension of Example 1 was hydrothermally treated using different severity factors. This hydrothermal treatment was done by treating the yeast biomass suspension in closed pressure reactor (1 liter Parr reactor, stirring 500 rpm) for a determined temperature and time, cooled to room temperature. Biomass solids were filtered from the treated yeast biomass suspension with Buchner filter (2 um filter) and the separated solids were dried to solids dry matter content of 95%.

The biomass solids from each hydrothermal treatment were milled to powder in a Retch laboratory mill. The milled solids were extracted with heptane at 50° C. (solids/heptane ratio 1:5 w/w) for 1 hour, centrifuged to separate solids and solvent-oil phase. The solids were additionally washed with fresh heptane, centrifuged and the separated solvent-oil phase was combined with the solvent-oil phase from the extraction step. The solvent was evaporated to obtain a crude microbial oil fraction.

The extraction yields from original dried yeast biomass (named "no HTT") and hydrothermally treated biomasses are presented in Table 4. As can be seen from Table 4, the oil yield from original dried biomass is low due to inefficient cell disruption. Treating biomass at 140° C./15 min is also not enough to disrupt cells and oil yield is likewise poor. After HTT at severe enough conditions (log R0>3.6), all oil in biomass can be extracted.

When the reaction temperature is 140° C., the pressure is about 5 bar. When the temperature is 160° C., the pressure is 6.2 bar to 6.8 bar. When the temperature is 180° C., the pressure is 10.3 bar to 11.0 bar. When the temperature is 210° C., the pressure is 19.6 bar.

TABLE 4

Oil yields from *Rhodosporidium toruloides* yeast grown on pure sugar after different hydrothermal treatments, oil extracted with heptane.

| Hydrothermal treatment | Severity, $LogR_0$ | Oil yield (% of oil in original biomass) |
| --- | --- | --- |
| no HTT | 0 | 25% |
| 140° C./15 min | 2.6 | 26% |
| 160° C./3 h | 4.0 | 101% |
| 180° C./30 min | 4.0 | 100% |
| 180° C./1 h | 4.2 | 98% |
| 210° C./0 min | 4.5 | 103% |

*Oil in original biomass = total fatty acids analysed by GC.

Example 6

Effect of Hydrothermal Treatment on Quality of Oil Extracted from Yeast Biomass

The impurities were analysed form three sets of crude microbial oils. In the first comparative example, the crude microbial oils extracted from *Rhodosporidium* biomass as described in previous Example 5 were analysed for impurities (metals, phosphorus) by ICP.

In the second comparative example, crude microbial oils from *Cryptococcus* biomass batches 1 and 2 grown on pure sugars as described in Example 3 and similarly hydrothermally treated as the *Rhodosporidium* biomasses in Example 5, were analysed for the same impurities.

In the third comparative example, crude microbial oils from *Rhodosporidium* biomasses batch 1 and 2 grown on lignocellulosic sugars as described in Example 2 and similarly hydrothermally treated as the *Rhodosporidium* biomasses in Example 5 were analysed for the impurities.

Oil extracted from the hydrothermally treated biomass has as good quality as the oil from non-hydrothermally treated biomass. In terms of some impurities (P, Ca, Mg and N), the hydrothermally treated oil is even purer than the microbial oil, which has not been subjected to hydrothermal treatment, as can be seen from the analyses results presented in Tables 5, 6 and 7. For both the yeast *Cryptococcus* and *Rhodosporidium*, thermal harvesting seems to be very effective in producing oil with negligible amounts of metals and phosphorus and thus minimal pre-treatment is needed before catalytic conversion of microbial oil to fuels or chemicals.

By changing the hydrothermal treatment conditions, especially the temperature, it is possible to change the oil quality. By lowering the temperature less nitrogen compounds are introduced to the oil, although, the content of nitrogen in the waste water is as high as in heat treatments done at a higher temperature.

TABLE 5

Comparison between microbial oil extracted from hydrothermally treated and non-hydrothermally treated sugar grown *Rhodosporidium toruloides* biomass of Example 5

| HTT conditions | | No HTT | 140 C./ 15 min | 160 C./ 3 h | 180 C./ 30 min | 180 C./ 60 min | 210 C./ 0 min |
| --- | --- | --- | --- | --- | --- | --- | --- |
| Severity, $LogR_0$ | | 0 | 2.6 | 4.0 | 4.0 | 4.2 | 4.5 |
| N | mg/kg | 290 | 320 | 64 | 200 | 120 | 190 |
| Fe | mg/kg | <0.1 | <0.1 | <0.3 | <0.1 | <0.1 | 0.1 |
| Na | mg/kg | 33.9 | 64.2 | 6.2 | 46.4 | 8.7 | 1.2 |
| Si | mg/kg | 1.3 | 94.4 | 1.7 | 4.1 | 5.3 | 2 |
| Ca | mg/kg | 3.4 | 6.3 | 1 | 2.7 | 2 | 0.4 |
| Mg | mg/kg | 3.9 | 9.1 | 2.8 | 10.4 | 3.4 | 0.7 |
| P | mg/kg | 396 | 673 | 54.8 | 363 | 108 | 29.2 |

TABLE 6

Comparison between microbial oil extracted from hydrothermally treated and non-hydrothermally treated sugar grown *Cyptococcus curvatus* biomass of Example 3

| HTT conditions | | Biomass batch 1 140 C./ 60 min | Biomass batch 2 160 C./ 3 h | Biomass batch 1 180 C./ 60 min | Biomass batch 1 180 C./ 0 min | Biomass batch 1 180 C./ 30 min |
| --- | --- | --- | --- | --- | --- | --- |
| Severity, $LogR_0$ | | 2.6 | 4.0 | 4.2 | 3.2 | 3.9 |
| N | mg/kg | N.A. | 92 | N.A. | 360 | 500 |
| Fe | mg/kg | 0.2 | <0.1 | <0.1 | <0.1 | <0.1 |
| Na | mg/kg | 122 | <1.0 | 1.4 | 1.9 | 1.9 |
| Si | mg/kg | 49 | 1.5 | 3.5 | 2.6 | 5.8 |
| Ca | mg/kg | 87 | <0.3 | <0.3 | <0.3 | <0.3 |
| Mg | mg/kg | 95 | <0.3 | <0.3 | <0.3 | <0.3 |
| P | mg/kg | 674 | 0.8 | 1 | 0.7 | <0.6 |

TABLE 7

Comparison between microbial oil extracted from hydrothermally treated and non-hydrothermally treated lignocellulose grown *Rhodosporidium toruloides* biomass of Example 2.

| HTT conditions | | Biomass Batch 1 Pasteurized, no HTT | Batch 1 180 C./ 60 min | Batch 1 180 C./ 60 min | Batch 2 No HTT | batch 2 180 C./ 60 min |
| --- | --- | --- | --- | --- | --- | --- |
| Severity, $LogR_0$ | | 0 | 4.2 | 4.2 | 0 | 4.4 |
| Wash of biomass | | unwashed bm | unwashed bm | washed bm | unwashed biomass | unwashed biomass |
| N | mg/kg | NA | 200 | 52 | 1500 | 210 |
| K | mg/kg | NA | NA | NA | 25000 | 0.69 |
| Fe | mg/kg | 1.3 | <0.1 | <0.1 | 2.6 | <0.1 |
| Na | mg/kg | 132 | 5.5 | <1.0 | 120 | <1.0 |
| Si | mg/kg | 17.4 | 11.1 | 3.8 | 97 | 6.2 |
| Ca | mg/kg | 13.5 | 2.2 | <0.3 | 750 | <0.3 |
| Mg | mg/kg | 79.2 | 2.3 | <0.3 | 150 | <0.3 |
| P | mg/kg | 1800 | 38.5 | 0.7 | 1800 | 2.3 |
| Mn | mg/kg | <0.3 | <0.3 | <0.3 | 26 | <0.3 |

Example 7

Effect of Hydrothermal Treatment on Removal of Dissolved Lignocellulose Material from Water Phase with Yeast Grown on Lignocellulose Hydrolysate

*Rhodosporidium toruloides* yeast suspension Batch 1 of Example 2 was hydrothermally treated in laboratory scale at different severities. After this processing the solids were removed by filtration thus creating a supernatant liquid stream. As a first comparative case the liquid supernatant was recovered from the yeast suspension without hydrothermal treatment by centrifugation and without pasteurization of the suspension ("no HTT" in Table 8). As a second comparative case the yeast suspension was first pasteurized and liquid supernatant was recovered from the yeast suspension without hydrothermal treatment by centrifugation ("Pasteurization 105 C/5 min" in Table 8).

Table 8 shows how the characteristics of the supernatant are varied by different processing conditions. Supernatant Chemical oxygen demand (COD) of the liquid supernatant was lowered by 21% in hydrothermal treatment of the yeast suspension at 180° C./1 h and by 47% in hydrothermal treatment at 250° C./1 h. The higher the severity of the hydrothermal treatment the more dissolved material present in the cultivation media was solidified during the treatments and could be recovered with the yeast biomass by filtration. In contrast, mere pasteurization releases material from the biomass to the liquid thus creating more dissolved material as shown in Table 8 on row named "DW-% of the initial".

Not all of the dissolved material is transferred to separable solid biomass fraction as part of the dissolved material and biomass is also gasified during the thermal treatment. The amount of gases is 2-5% of the initial dry matter and the gases consist mostly of carbon monoxide, carbon dioxide, oxygen and various hydrocarbons.

Example 8

Effect of Washing of Hydrothermally Treated Microbial Biomass on Quality of the Extracted Oil This example shows that a water wash of the hydrothermally treated yeast biomass prior to oil extraction effectively lowers the amount of nitrogen and metals in the oil as shown in Table 9. This is very beneficial and significantly decreases the need for purification and may even eliminate the need for the pre-treatment step before catalytic conversion of crude microbial oil to fuels or chemicals.

TABLE 9

Comparison between yeast oil extracted from hydrothermally treated biomass without and with water washing

| Biomass | *Rhodosporidium toruloides*, lignocellulose cultivation batch 1 | | *Cryptococcus curvatus*, sugar cultivation batch2 | | *Cryptococcus curvatus*, sugar cultivation batch 3 | |
|---|---|---|---|---|---|---|
| HTT | 180° C./60 min, $LogR_0 = 4.2$ | | 190° C./60 min, $LogR_0 = 4.5$ | | 160° C./3 h, $LogR_0 = 4.0$ | |
| Wash of biomass | Un-washed | washed | Un-washed | washed | un-washed | washed |
| N mg/kg | 200 | 52 | 400 | 180 | 140 | 56 |
| Fe mg/kg | <0.1 | <0.1 | <0.1 | <0.1 | <0.1 | <0.1 |
| Na mg/kg | 5.5 | <1.0 | <1.0 | <1.0 | 1 | <1.0 |
| Si mg/kg | 11.1 | 3.8 | 10.9 | 8.3 | 1.7 | 2.1 |
| Ca mg/kg | 2.2 | <0.3 | <0.3 | 0.4 | <0.3 | <0.3 |
| Mg mg/kg | 2.3 | <0.3 | <0.3 | <0.3 | <0.3 | <0.3 |
| P mg/kg | 38.5 | 0.7 | <0.6 | <0.6 | <0.6 | <0.6 |

Example 10

Effect of Drying and Oil Extraction Temperatures on Quality of the Extracted Oil It has been found that the amount of impurities in the extracted microbial oil, especially the amount of nitrogen can be adjusted by optimizing the drying of the biomass before the oil extraction step (Table 10) and by optimizing the oil extraction temperature (Table 11). The results show that the lower drying and extraction temperatures are beneficial for the quality of the extracted oil.

TABLE 8

Analysis results on the separated supernatant liquids after hydrothermal treatment at different conditions.

| Hydrothermal treatment | No HTT | No HTT, pasteurization 105 C./ 5 min | 180 C./ 1 h | 190 C./ 1 h | 220 C./ 20 min | 250 C./ 1 h | 180 C./ 1 h |
|---|---|---|---|---|---|---|---|
| Severity, $LogR_0$ | 0 | 1.2 | 4.2 | 4.5 | 5.2 | 6.3 | 4.4 |
| BRIX | 10.8 | 11.1 | 8.7 | 7.5 | 7.1 | 4.93 | 8.1 |
| DW-% | 9.30% | 10.18% | 7.76% | 6.77% | 6.21% | 5.90% | 7.10% |
| TOC-mg/l C | 32500 | 34500 | 25800 | 23000 | 21100 | 16200 | 26300 |
| COD-mg/l | 87000 | 91000 | 69000 | 62000 | 57000 | 4600 | 66000 |
| N-mg/l | 1400 | 1600 | 1400 | 1300 | 1400 | 1100 | 1400 |
| DW-% of initial | 100.0% | 109.5% | 83.4% | 72.8% | 66.8% | 63.4% | 76.3% |
| OC-% of initial | 100.0% | 106.2% | 79.4% | 70.8% | 64.9% | 49.8% | 80.9% |
| COD-% of initial | 100.0% | 104.6% | 79.3% | 71.3% | 65.5% | 52.9% | 75.9% |
| N-% of initial | 100.0% | 114.3% | 100.0% | 92.9% | 100.0% | 78.6% | 100.0% |

TABLE 10

Comparison between microbial oil extracted from hydrothermally treated yeast biomasses using n-hexane after using different drying conditions.

*Rhodosporidium toruloides*, lignocellulose cultivation batch 1, thermal harvesting @180° C./1 h

|  |  | lyophilized | 85 C. (oven over night) | 120 C. (contact dryer) |
|---|---|---|---|---|
| Nitrogen | mg/kg | 230 | 220 | 650 |
| Fe | mg/kg | <0.1 | <0.1 | <0.1 |
| Na | mg/kg | 2.3 | <1.0 | 1.1 |
| Si | mg/kg | 10.8 | 4.1 | 4.5 |
| Ca | mg/kg | 1.4 | 0.4 | 0.4 |
| Mg | mg/kg | 1.2 | 0.3 | 0.4 |
| P | mg/kg | 10.7 | 2.3 | 4.3 |

TABLE 11

Comparison between microbial oil extracted from hydrothermally treated yeast biomasses in different extraction temperatures using n-heptane as solvent

|  |  | *Cryptococcus curvatus*, pure sugar cultivation, thermal harvesting @180 C./1 h | | | *Rhodosporidium toruloides*, lignocellulose cultivation batch 1, thermal harvesting @180 C./1 h | | |
|---|---|---|---|---|---|---|---|
|  |  | RT | 50 C. | 90 C. | RT | 50 C. | 90 C. |
| Nitrogen | mg/kg | 67 | 80 | 84 | 160 | 180 | 190 |
| Fe | mg/kg | <0.1 | <0.1 | <0.1 | <0.1 | <0.1 | <0.1 |
| Na | mg/kg | <1.0 | <1.0 | <1.0 | <1.0 | <1.0 | <1.0 |
| Si | mg/kg | 1.8 | 1.9 | 1.7 | 3.7 | 3.2 | 2.9 |
| Ca | mg/kg | <0.3 | <0.3 | <0.3 | 0.4 | 0.5 | <0.3 |
| Mg | mg/kg | <0.3 | <0.3 | <0.3 | 0.3 | 0.5 | <0.3 |
| P | mg/kg | 1.7 | 1.5 | 1.8 | 3 | 3.5 | 1.7 |

The results of this example shows that the by drying of the hydrothermally treated biomass at temperatures lower than 85° C. the amount of nitrogen in the extracted microbial oil can be significantly lowered. It is also shown that by conducting the oil extraction at room temperature the amount of nitrogen in the extracted microbial oil is furthermore reduced compared to extraction at higher temperatures.

Example 11

Effect of pH Adjustment on the Hydrothermal Harvesting and Quality of Extracted Oil During the hydrothermal harvesting it is seen that the pH of the suspension naturally decreases as can be seen from Table 12. It is also possible to adjust the pH of the suspension before hydrothermal harvesting, which increases the amount of biomass that becomes soluble in the suspension during the heating period. With some tested yeasts biomasses the making the biomass more acidic before HTT makes the yeast cells float at shorter treatment times and at lower temperatures. Though, this earlier and easier flotation does not change the severity needed to make these yeasts filterable and thus pH adjustment creates an advantage only if the separation of the yeast cells with centrifugation is deemed necessary. It should be noted that in this case the severity factor is not high enough to enable efficient disruption of the cells and thus the oil yield remains low.

Adjustment of the pH can also have an effect on the quality of the final oil. In Table 13 the severity factor of the hydrothermal treatment for both of the biomass suspensions has been the same, but the pH of the other biomass suspension has been adjusted acidic before hydrothermal treatment. The nitrogen content of the oil extracted from the latter biomass is slightly higher.

TABLE 12

Effect of pH adjustment of the biomass suspensions (*Rhodosporidium toruloides* cultivated on sugar) before HTT on the dissolution rate of the biomass into the liquid phase.

|  | HTT @180° C., 60 min | | HTT @180 C., 60 min: pH of the suspension adjusted to 4 using acetic acid | |
|---|---|---|---|---|
| T, ° C. | pH | solid bm (% of initial) | pH | solid bm (% of initial) |
| 25 | 5.75 | 100% | 4 | 100% |
| 100 | 5.8 | 85% | 3.97 | 78% |
| 110 | 5.79 | 84% | 3.67 | 76% |
| 120 | 5.66 | 82% | 3.66 | 74% |
| 130 | 5.58 | 82% | 3.64 | 71% |
| 140 | 5.33 | 82% | 3.55 | 69% |
| 150 | 5.23 | 82% | 3.43 | 62% |
| 160 | 5.09 | 80% | 3.45 | 55% |
| 170 | 5.01 | 75% | 3.47 | 50% |
| 180-0 min | 4.83 | 64% | 3.52 | 46% |
| 180-10 min | 4.63 | 55% | 3.62 | 50% |
| 180-30 min | 4.45 | 58% | 3.54 | 53% |
| 180-60 min | 4.24 | 62% | — | — |

TABLE 13

Effect of pH adjustment of the biomass suspension (*Cryptococcus curvatus* cultivated on sugar, batch 2) before HTT on the oil quality.

|  |  | HTT @180 C./60 min | HTT @180 C./60 min; pH of the suspension adjusted to 3 with acetic acid |
|---|---|---|---|
| Nitrogen | mg/kg | 120 | 190 |
| Fe | mg/kg | <0.1 | <0.1 |
| Na | mg/kg | <1.0 | <1.0 |
| Si | mg/kg | 1.3 | 1.4 |
| Ca | mg/kg | <0.3 | 0.3 |
| Mg | mg/kg | <0.3 | <0.3 |
| P | mg/kg | <0.6 | 0.8 |

The invention claimed is:

1. A method for recovery of microbial lipids from oleaginous yeast biomass, said method comprising:
   (i) providing an aqueous suspension including fermentation broth containing oleaginous yeast biomass;
   (ii) subjecting said suspension to a hydrothermal treatment at a temperature of at least 160° C. for 1 second to 360 minutes at a pressure above 5 bar;
   (iii) subjecting the hydrothermally treated suspension to a separation step to obtain a liquid fraction and a yeast biomass fraction;
   (iv) subjecting the yeast biomass fraction to a drying step to obtain a dried yeast biomass fraction, wherein the temperature of the drying step is below 85° C.;
   (v) subjecting the dried biomass fraction to an extraction step with a liquid solvent to produce a liquid fraction containing microbial lipids and a solid fraction containing residual yeast biomass fraction, wherein the extraction step is conducted at room temperature;

(vi) recovering the microbial lipids from the liquid fraction of step (v); and
(vii) optionally, isolating a residual biomass fraction from a product of step (v).

2. The method according to claim 1, comprising:
obtaining the fermentation broth from cultivation of oleaginous yeasts in a cultivation medium containing lignocellulose hydrolysate.

3. The method according to claim 2, comprising:
washing the separated yeast biomass fraction in step (iii) with water prior to the drying in step (iv) and/or the extraction in step (v).

4. The method according to claim 3, wherein the yeast biomass fraction obtained from the separation step has a dry matter content of at least 50%.

5. The method according to claim 4, wherein the dried biomass fraction has a dry matter content of at least 90%.

6. The method according to claim 5, comprising:
conducting the hydrothermal treatment under conditions corresponding to a severity factor Log $R_0$ of at least 3.5.

7. The method according to claim 6, comprising:
conducting the hydrothermal treatment under conditions corresponding to a severity factor Log $R_0$ of about 3.5 to about 5.5.

8. The method according to claim 7, wherein the yeast biomass has a lipid content of at least 20% by weight of cell mass.

9. The method according to claim 8, wherein the aqueous suspension has a dry matter content of at least 3%.

10. The method according to claim 8, wherein the yeast is of genus *Rhodosporidium*, *Rhodotorula*, *Lipomyces*, *Cryptococcus* or *Saccharomyces*.

11. The method according to claim 6, comprising:
conducting the extraction step (v) at a temperature of below about 90° C.

12. The method according to claim 6, comprising:
conducting the hydrothermal treatment in step (ii) at a temperature range of about 180° C. to about 210° C.

13. The method according to claim 6, comprising:
conducting the hydrothermal treatment in step (ii) at temperatures and pressure distributed according to when a reaction temperature is about 160° C., and the pressure is about 6.2 bar to about 6.8 bar.

14. The method according to claim 3, wherein the yeast biomass fraction obtained from the separation step has a dry matter content of at least 60%;
wherein the dried biomass fraction has a dry matter content of at least 95%;
wherein the yeast biomass has a lipid content of at least 35% by weight of cell mass;
wherein the aqueous suspension has a dry matter content of at least 10%; and
wherein the yield of the extracted oils or lipids is in a range of at least about 100% based on the content of the oils or lipids present in the biomass;
the method comprising:
conducting the hydrothermal treatment under conditions corresponding to a severity factor Log $R_0$ of at least 3.9;
conducting the hydrothermal treatment under conditions corresponding to a severity factor Log $R_0$ of about 4.0 to about 4.5;
conducting the drying step (iv) in vacuum and at a temperature of the biomass of below 70° C.;
conducting the extraction step (v) at a temperature of below about 70° C.;
wherein the pH value of the aqueous suspension in step (i) is below about 5;
conducting the hydrothermal treatment in step (ii) at a pressure in the range of about 10 to about 25 bar;
conducting the hydrothermal treatment in step (ii) at temperature range of about 190° C. to about 200° C.; and
conducting the hydrothermal treatment in step (ii) at temperatures and pressure distributed according to when a reaction temperature is about 160° C., and the pressure is about 19.6 bar.

15. The method according to claim 1, wherein the separation (iii) is performed by centrifugation or involves a step of centrifugation.

16. The method according to claim 1, wherein the separation (iii) is performed by filtration or involves a step of filtration.

17. The method according to claim 1, comprising:
conducting the drying step (iv) in vacuum and at a temperature of the biomass of below 90° C.

18. The method according to claim 1, wherein the pH value of the aqueous suspension in step (i) is below about 6.

19. The method according to claim 1, wherein the method does not comprise an extraction of the separated liquid fraction in step (iii).

20. The method according to claim 1, comprising:
conducting the hydrothermal treatment in step (ii) at a pressure in range of about 6 to about 25 bar.

21. The method according to claim 1, wherein the yield of the extracted oils or lipids is in a range of at least about 70% based on a content of oils or lipids present in the biomass.

* * * * *